United States Patent [19]

Kehm

[11] 4,073,886
[45] Feb. 14, 1978

[54] BLOOD FRACTIONATION PROCESS USING BLOCK COPOLYMERS OF ETHYLENE OXIDE AND POLYOXYPROPYLENE

[75] Inventor: Walter C. Kehm, Scarsdale, N.Y.

[73] Assignee: Baxter Travenol Laboratories, Inc., Deerfield, Ill.

[21] Appl. No.: 327,892

[22] Filed: Jan. 30, 1973

[51] Int. Cl.² .................. A61K 37/02; C07G 7/00
[52] U.S. Cl. .................. 260/112 B; 424/101; 424/177
[58] Field of Search .................. 260/112 B

[56] References Cited

U.S. PATENT DOCUMENTS

| | | | |
|---|---|---|---|
| 2,390,074 | 12/1945 | Cohn | 260/112 B X |
| 2,631,018 | 12/1971 | Shanbrom et al. | 260/112 B |
| 3,415,804 | 12/1968 | Polson | 260/112 B |
| 3,450,502 | 6/1969 | Hymes | 23/258.5 |
| 3,560,475 | 2/1971 | Fekete et al. | 260/112 B |
| 3,577,522 | 5/1971 | Hymes | 424/78 |
| 3,652,530 | 3/1972 | Johnson et al. | 260/112 B |
| 3,682,881 | 8/1972 | Fekete et al. | 260/112 B |
| 3,770,631 | 11/1973 | Fekete et al. | 210/53 |

FOREIGN PATENT DOCUMENTS

| | | |
|---|---|---|
| 2,231,676 | 1/1973 | Germany. |
| 1,366,246 | 9/1974 | United Kingdom. |

*Primary Examiner*—Howard E. Schain
*Attorney, Agent, or Firm*—Paul C. Flattery; Lawrence W. Flynn; Max D. Hensley

[57] ABSTRACT

A method of separating proteinaceous and lipid materials from blood serum and plasma which comprises selective precipitation with block copolymers of ethylene oxide and polyoxypropylene polymer.

7 Claims, No Drawings

BLOOD FRACTIONATION PROCESS USING BLOCK COPOLYMERS OF ETHYLENE OXIDE AND POLYOXYPROPYLENE

This invention relates to a method of separating proteinaceous and lipid materials from blood serum and plasma.

Blood comprises a fluid containing the red and the white blood cells and the blood platelets. The plasma, or fluid part of blood, contains about 90% water and 10% solids. These solids consist essentially of about 7-9% proteins, 1% salts, and the remainder lipids and other substances. Freshly drawn blood clots within a few minutes. Formation of the clot is a complex process in which the protein, fibrinogen, is converted into insoluble fibrin. Blood serum is plasma from which this fibrin has been removed.

Fractionation of blood plasma and serum and the laboratory and clinical use of the separated blood components is common practice today. Among the various components separated from blood are albumin, $\alpha_1$-globulins, $\alpha_2$-globulins, $\beta$-globulins, $\gamma$-globulins, fibrinogen, prothrombin, antihemophilic globulin, lipoproteins, thromboplastin, complement components, isoagglutinins, cholesterol, phosphatides, and numerous enzymes, e.g., amylase, fibrinolysin, esterase, and phosphatase. Various methods have been developed heretofore for separating and purifying the foregoing and other blood components. These methods generally comprise one or more of the following procedures:

(a) fractional precipitation with ammonium sulfate and similar salts;

(b) organic solvent precipitation with cold ethanol or acetone and other such alcohols and ketones;

(c) selective adsorption on calcium phosphate gels or with barium sulfate;

(d) isoelectric precipitation by pH adjustment to the point at which there is no net charge on a given protein; and (e) chromatography by use of adsorbents such as CM- or DEAE-cellulose or by "Sephadex" gel filtration.

Other more recently developed procedures for selectively fractionating and purifying blood proteins involve the use of amino acids such as glycine and beta alanine, water-soluble organic polymers such as polyethylene glycol and polypropylene glycol, and water-insoluble polyelectrolyte polymers containing basic amino groups such as the dimethylaminopropylimide group.

Among these various previously used polymers, the polyethylene glycols disclosed in general as blood protein precipitants by Albertsson, "Partition of Cell Particles and Macromolecules," John Wiley & Sons, Inc., Stockholm and New York, 1960, and further described by Polson et al., *Biochim. Biophys. Acta* 82, 463-75 (1964) and U.S. Pat. No. 3,415,804, have been found to be highly useful in blood fractionation procedures. While these polymers provide good separation of components and are essentially non-toxic to the human, they do not have the optimun solubility and stability desired in practice and it is preferable to remove as much as possible of the polymer from the separated fraction prior to human administration.

In accordance with the present invention, a new and improved method is provided for separating proteinaceous and lipid materials from blood serum and plasma. The method comprises selective precipitation with certain block copolymers which are ethylene oxide-propylene glycol condensation products. Separation of the blood components with these block copolymers has been found to be substantially and significantly better than with the polymeric polyethylene glycol. These improvements consist of increased yield and higher purity of the precipitated protein substances, greater clarity and stability of the resulting supernatant liquid serum products, and more rapid separation of the desired components.

Use of these block copolymers in accordance with the present invention has the further advantage in that not only is it unnecessary to remove essentially all the polymer from the separated blood fraction prior to its human administration, but also it is desirable to retain a small amount thereof in said fraction. Presence of a residual amount of the block copolymer, for example, 1-2% or even a fraction of a percent, facilitates greater acceptability of the administered blood protein and faster assimilation throughout the body and/or organ.

Although it is not intended to be bound by theory, it is believed that the aforementioned effectiveness of the block copolymers in accordance with the present invention is due, at least in part, to their formation of association complexes with the blood proteins by hydrogen bonding which involves a hydroxyl group of the glycol moiety in the polymer and a non-labile hydrogen of the protein.

The ethylene oxide-propylene glycol condensation products employed in this invention can be prepared by condensing ethylene oxide with polyoxypropylene polymer. A further description of the preparation of these block copolymers is found in U.S. Pat. No. 2,674,619. These block copolymers can be represented by the following structural formula:

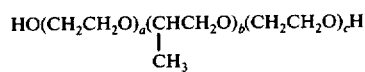

For purposes of this invention, these block copolymers desirably contain at least 50% ethylene oxide in the molecule and a polyoxypropylene hydrophobic base having a molecular weight of at least 900 and preferably between 950 and 1750. Materials containing less than 50% ethylene oxide are not sufficiently non-toxic and products having a hydrophobic base molecular weight less than 900 do not have the desired solubility. In this respect, the block copolymers employed in this invention are related to and include materials used as blood plasma substitutes and for priming heart-lung apparatus as described in U.S. Pat. Nos. 3,450,502; 3,577,522 and 3,590,125, herewith incorporated by reference. Said materials are described in U.S. Pat. No. 3,450,502 as compounds having the formula $HO(C_2H_4O)_b(C_3H_6O)_a(C_2H_4O)_bH$ wherein a is an integer such that the hydrophobe base represented by $(C_3H_6O)$ has a molecular weight of at least 950 and b is an integer such that the hydrophile portion represented by $(C_2H_4O)$ constitutes from about 50% to 90% by weight of the compound.

Illustrative examples of suitable block copolymers such as "PLURONIC" polyols sold by Wyandotte Chemicals Corp. having an average molecular weight from about 2000 to about 16,000 as exemplified by grade F-38 which contains about 80% of polyoxyethylene hydrophilic units in the molecule and the polyoxypropylene hydrophobic base has a molecular weight of 950 and by grade F-68 which also contains 80% of polyoxyethylene hydrophilic units in the molecule but the hydrophobic base has a molecular weight of 1750. The average molecular weight of these two "PLURONIC" polyols is 4750 and 8750, respectively. A further description of these polyols is found in the bulletin of Wyandotte Chemicals Corp. "The Pluronic Grid", Sixth Edition, also incorporated herein by reference.

The amount of block copolymer employed in the separation process of this invention can vary, depending in part on the particular proteinaceous or lipid fraction to be precipitated from the blood plasma or serum. In general, from about 1% to about 35% of the copolymer on a basis of weight per volume of the plasma or serum is employed, sufficient to precipitate that fraction. Relatively low levels of the block copolymer, for example, from about 1% to about 20% are generally employed for fractionating specific protein materials which are desired to be retained for laboratory and clinical use, such as, for example, the various blood plasma factors. Higher levels of the block copolymer, for example, from greater than about 20% to about 30%, are preferred for removing substantially all undesired proteinaceous and lipid particulate matter from the blood plasma or serum. This is achieved by precipitating a product at this concentration of copolymer which can be separated from said particulate matter, which is soluble and remains in the supernatant. The precipitate can then be redissolved to form a crystal clear serum.

Product precipitation can be conducted by a sequence of steps in which the concentration of the block copolymer is adjusted to various suitable levels for fractionating a series of the desired components from the starting blood serum or plasma. Separation of the desired components at any given step can then be carried out by conventional means such as by filtration, centrifugation, decantation and the like procedures.

The precipitation can be conducted at ordinary room temperature (about 25° C) but colder temperatures are generally preferred since proteinaceous materials are known to be subject to heat denaturation and optimum potency is retained in the proteinaceous material by maintaining cold temperatures of from about 4° to about 25° C.

Redissolution of the precipitate can be carried out by admixing with a compatible medium, generally a physiologically acceptable medium such as water, saline, citrated saline, glycine citrated saline and other such aqueous media in any desired amount, depending upon the desired concentration of the separated blood component in the mixture.

The separated blood component can also be dried such as by freeze drying, lyophilization and the like means to provide a storage stable product which can be reconstituted prior to use.

The method of the present invention can also be used in combination with other blood fractionation procedures, such as for example, the prior art procedures described hereinbefore. Thus, in some instances it is useful to employ the block copolymer agents in combination with certain other substances which are essentially precipitation or absorption agents. In particular, glycine, tricalcium phosphate and diatomaceous earth are frequently advantageously employed in conjunction with the block copolymers. The step in the separation process at which these other agents are ecployed and the amounts used will vary, depending in part on the particular proteinaceous or lipid material desired to be precipitated. Generally, from about 0.5% to 2% of the tricalcium phosphate, about 0.1% to 0.5% of the diatomaceous earth, and about 2 to 3 molar glycine are suitable in these instances.

Other precipitation agents such as methanol, ethanol, ether and polyethylene glycol and other absorption agents such as aluminum hydroxide and the like materials which can be used in combination with the method of the present invention will be apparent to those skilled in the art.

The following specific examples will illustrate the invention at it applies in particular to the preparation of anti-hemophilic globulin and prothrombin coagulation factors, to thromboplastin controls, and to the preparation of clarified serums for organ perfusates and for use as blood grouping and typing serums. It will be appreciated that other examples will be apparent to those skilled in the art and the invention is not limited to these specific illustrative examples.

EXAMPLE 1

The preparation of plasma for use as an organ perfusion fluid

Plasma that has been collected in anticoagulant is first treated by admixing with glycine to a molarity of 2 to 3 respective of glycine at pH 6.88 in the cold (8° C) for 30 to 45 minutes. The precipitate that forms is discarded and the remaining supernatant fluid is diluted 1:1 with normal saline (0.85% NaCl solution). From above 20% to about 30% (wt./vol.) of "PLURONIC" F-38 is then added at pH 6.5 to 7.0 and the mixture stirred for 30 minutes at room temperature. The supernatant fluid is discarded and the remaining precipitate dissolved in normal saline solution to a level of approximately the original plasma volume. To this solution is added 0.5% (wt./vol.) of tricalcium phosphate at pH 7.2. The suspension is mixed for 15-60 minutes at room temperature (25° C). The precipitate that is formed is discarded and the supernatant fluid is retained. To the supernatant fluid is added sodium citrate to a concentration of 0.02 M. The pH is adjusted to 7.5 and the fluid is then heat treated at 37° C for 24 to 120 hours until the level of coagulation Factor V (proaccelerin) is decreased to approximately zero percent. Then 0.15% (wt./vol.) "CELITE" diatomaceous earth filter aid is added and the fluid mixed for 10 minutes at room temperature. The resulting precipitate is discarded and the remaining supernatant fluid is sterile filtered through a "MILLIPORE" filter (0.3 microns). The retained fluid is stable in storage and is crystal clear in appearance. It is eminently suitable for use as an organ perfusion fluid, for example, a kidney, heart or lung perfusion fluid.

In the above Example, the glycine precipitation step removes essentially all the Factor VIII and fibrinogen, the "PLURONIC" F-38 precipitation step removes essentially all the lipoprotein and residual fibrinogen, the tricalcium phosphate absorption step removes Factors II, VII, IX and X, the heating at 37° C inactivates Factor V and the "CELITE" absorption step removes Factors XI and XII.

EXAMPLE 2

The preparation of serum for use as blood grouping and typing serums

The serum to be clarified is first diluted with normal saline (0.85% NaCl solution) so that the protein concentration is between about 2.5 and 3.0 grams/100 ml. The pH is adjusted to 6.5-7.0 and then from above 20% to about 30% of "PLURONIC" F-38 (preferably about 24 grams/80 ml.) is added at room temperature and mixed for 30 to 60 minutes. The supernatant, which contains lipoprotein and fibrous materials, is discarded and to the remaining precipitate is added sufficient normal saline to adjust the volume to a level of about the original serum volume. The pH is adjusted to 7.2 and then 0.5% (wt./vol.) of tricalcium phosphate is added to the dissolved precipitate. The suspension is mixed for 30 minutes at room temperature. The mixture is then centrifuged to clarify the serum and the resulting supernatant serum is carefully decanted from the tricalcium phosphate and activated clotting factors complex and retained for blood banking use. This procedure is suitable, for example, for the clarification of (a) Anti-A and Anti-B blood grouping serums, and (b) Anti-c̄ and Anti-ē typing serums for the saline tube test.

EXAMPLE 3

The preparation of an AHF concentrate for clinical use

To prepare a potent antihemophilic factor (AHF, Factor VIII) concentrate by fractionation with "PLURONIC" F-38, the following procedure is followed:

Whole blood is collected in 4% citrate anticoagulant solution (1 part of 4% citrate anticoagulant solution plus 9 parts of whole blood); the cells are separated from the plasma by centrifugation; the retained plasma is frozen at -25° C and then thawed at 4°-5° C; and the resulting cryoprecipitate is collected by centrifugation.

The cryoprecipitate is dissolved in 0.1 molar glycine-citrated saline (one part 0.1M sodium citrate in four parts by weight 0.9% saline made 0.1M respective of glycine) at 22-25° C (room temperature) and the pH is adjusted to 6.5 with 1 normal acetic acid. Solid "PLURONIC" F-38, 3.5% (wt./vol.), is added and the suspension mixed for 15 minutes at 22°-25° C. The mixture is centrifuged for 30 minutes at 5000 RPM and the resulting precipitate (fibrinogen) is discarded.

The AHF-rich supernatant is collected and the pH is adjusted to 6.88 with 1N NaOH. Solid "PLURONIC" F-38 is then added to a final concentration of 10% (wt./vol.) and the suspension is mixed for 15 minutes at 22°-25° C. The mixture is centrifuged for 30 minutes at 5000 RPM and the supernatant is discarded.

The remaining AHF precipitate obtained by the second centrifugation is dissolved in citrated saline (one part of 0.1M sodium citrate in four parts by weight 0.9% saline) to a final potency of 20 to 30 AHF units per ml. As used herein, an AHF unit is equivalent to the AHF activity in one ml. of pooled normal whole plasma. The dissolved product is sterile filtered with a "MILLIPORE" membrane filter using pore sizes of 0.3μ, 0.45μ, and 0.2μ. The filtered solution is then filled under aseptic conditions in 10 ml. to 30 ml. capacity vials, rapidly frozen and lyophilized. Upon reconstitution with sterile water, the final product is suitable for administration to hemophiliac patients suffering bleeding episodes.

EXAMPLE 4

The preparation of a prothrombin complex for clinical use

To prepare a potent prothrombin complex (Factor II plus other clotting factors) by fractionation with "PLURONIC" F-38, the following procedure is followed:

Cohn plasma fraction IV-1 is suspended in normal saline (0.9 NaCl solution) to a concentration of 10% (wt./vol.) and the pH is adjusted to 7.2. Tribasic calcium phosphate (500 grams) is then added to 50 liters of the fraction IV-1 suspension and the mixture is stirred for about 30 minutes. The suspension is then centrifuged and the supernatant is discarded. The retained precipitate is suspended in 0.1M trisodium citrate to a final volume of 5 liters. The suspension is centrifuged and the precipitate is discarded. The pH of the retained supernatant is adjusted to 7.2, "PLURONIC" F-38 is added to a final concentration of 5%, and the suspension stirred for about 15 minutes. The suspension is clarified by centrifugation, with retention of the supernatant and discarding of the precipitate. The pH of the retained supernatant is then adjusted to 5.2, and "PLURONIC" F-38 is added to a final concentration of 20%. The suspension is centrifuged and the precipitate that is recovered is dissolved in citrated saline to a volume of 5 liters. Heparin is added in an amount of one unit per ml., and the dissolved product is sterile filtered with a "MILLIPORE" membrane filter using pore sizes of 0.3μ, 0.45μ, and 0.2μ. The filtered solution is then filled under aseptic conditions in 10 ml. to 30 ml. capacity vials, rapidly frozen and lyophilized. Upon reconstitution with sterile water, the final product is suitable for administration to patients deficient in Factor II.

In Examples 3 and 4, above, it is found that separation of the respective desired protein precipitate is achieved more rapidly than is the case when polyethylene glycol 4000 is used in place of the "PLURONIC" F-38 and the yield of the final product is substantially increased.

EXAMPLE 5

The preparation of a thromboplastin control from plasma

Fresh human blood is collected in 4% sodium citrate anticoagulant solution (1 part of anticoagulant and 9 parts of whole blood). The resulting mixture is centrifuged at 3000 × G at 5° C. The resulting supernatant plasma is centrifuged again in the same manner as before and then frozen at −20° C. The plasma is thawed at room temperature (ca. 25° C) and diluted with 0.9% physiologically normal saline solution (1 part of plasma and 1 part of normal saline solution). The pH of the resulting solution is adjusted to 6.0-7.0 with 1N HCl. "PLURONIC" F-38 is then added to the solution to a final concentration of 30% to form a precipitate. After centrifugation, excess citrate and trace amounts of thromboplastic active material are removed in the supernatant, which is discarded.

The above-prepared plasma is then used to prepare several thromboplastin controls for use in making prothrombin time determinations such as by the Quick one-stage prothrombin time test or the modified Owren prothrombin test as described in the "Hyland Reference Manual of Coagulation Procedures", published by Hyland Laboratories, Los Angeles, Calif., pp. 10-14 (2d ed. 1964). These controls are made to resemble physiological plasma by employing as the sole buffering agent for the plasma (1) citrate-imidazole-normal saline buffer, or (2) oxalate-imidazole-normal saline buffer, consisting of the following components:

(1) Citrate-imidazole-normal saline buffer 0.9% NaCl solution
0.0135 molar ± 0.005 tri-sodium citrate
0.025% to 0.035% imidazole (2) Oxalate-imidazole-normal saline buffer 0.9% NaCl solution
0.0135 molar ± 0.005 sodium oxalate
0.025% to 0.035% imidazole By using the foregoing amounts of the citrate or oxalate anticoagulants in said buffer, undesirable activation of the clotting factors and thromboplastin generation are effectively prevented. Excess citrate and traces of thromboplastic active material are removed, as hereinbefore provided, by the initial employment of the "PLURONIC" F-38 treatment on the plasma. With these combined steps, maximum stabilization of the thromboplastin controls is achieved.

The citrate controls (100% and 20% controls) are prepared as follows:

For the 100% control, for precipitant paste from the "PLURONIC" F-38 treatment is dissolved in the citrate-imidazole-normal saline buffer to 50% to 70% of the original volume of the plasma.

For the 20% control, the precipitant paste from the "PLURONIC" F-38 treatment is dissolved in normal saline to 80% to 120% of the original volume of the plasma. Prothrombin-free human plasma is then prepared from the redissolved precipitant paste by adsorbing out the "prothrombin complex" (Factors II, VII, IX and X). This adsorption is achieved by adding tricalcium phosphate to a final concentration of 1% by weight, adjusting the pH to 7.2 ± 0.2 with 1 normal HCl, and mixing for about 30 to 45 minutes. The suspension is then centrifuged. The supernatant is buffered with 0.0135M ± 0.005 trisodium citrate and 0.025% to 0.035% imidazole, and the pH adjusted to 7.8 ± 0.2 with 1 normal NaOH. This solution is then mixed with the appropriate volume of the above-prepared 100% citrate control to provide the desired clotting times for the 20% control.

The 100% and 20% oxalate controls are prepared in the same manner as the above-prepared citrate controls except that 0.0135M sodium oxalate is used in place of 0.0135M trisodium citrate.

Various other examples and modifications of the foregoing examples will be apparent to those skilled in the art. For example, albumin, γ-globulins, fibrinogen and other blood components can also be obtained by employing the separation procedure of this invention. These and other such blood components can be obtained directly from blood serum and plasma or from blood fractions known to contain the components. Thus, fibrinogen can be obtained from Cohn Precipitate I, the γ-globulins can be derived from Cohn Precipitate II + III and albumin can be separated from Cohn Precipitate V. So also, equivalent amounts of "PLURONIC" F-68 can be substituted for the "PLURONIC" F-38 in the foregoing examples with substantially similar results. Still other examples will be apparent after reading the disclosure herein. All such further examples and modifications as come within the spirit and scope of the invention are included in the appended claims.

What is claimed is:

1. A process for fractionating blood serum and plasma comprising selective precipitation of said material by admixing with a precipitating amount from about 1% to about 35% on a weight per volume basis of a compound of the formula

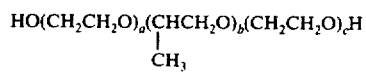

wherein $a$ and $c$ are integers such that the hydrophile portion represented by $(CH_2CH_2O)$ constitutes at least about 50% of the molecule and $b$ is an integer such that the hydrophobic portion represented by

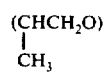

has a molecular weight of at least about 950.

2. The process of claim 1 in which the block copolymer contains about 80% of polyoxyethylene hydrophilic units in the molecule and the polyoxypropylene hydrophobic base has a molecular weight between about 950 and 1750.

3. The process of claim 1 in which blood coagulation factors are separated from serum and plasma by employing a concentration of the block copolymer of from about 1% to about 20%.

4. The process of claim 3 in which a concentrate of antihemophilic factor is obtained from cryoprecipitated plasma by admixing said cryoprecipitate in aqueous solution with about 3 to 5% by weight of the block copolymer, separating the resulting precipitate therefrom, admixing the retained supernatant with additional said block copolymer to a final concentration of about 10% and retaining the resulting precipitate as the desired concentrate.

5. The process of claim 4 in which the block copolymer contains about 80% of polyoxyethylene hydrophilic units in the molecule and the polyoxypropylene hydrophobic base has a molecular weight between about 950 to 1750.

6. The process of claim 3 in which a prothrombin complex is obtained from Cohn Fraction IV-1 by admixing said Fraction in aqueous solution with from about 0.5% to 2% tribasic calcium phosphate, suspending with resulting precipitate in aqueous solution of about 0.1 molar trisodium citrate, separating the remaining precipitate therefrom, admixing the retained supernatant with about 5% of the block copolymer, separating the resulting precipitate therefrom and admixing the retained supernatant with additional said block copolymer to a final concentration of about 20% and retaining the resulting precipitate as the desired prothrombin complex.

7. The process of claim 6 in which the block copolymer contains about 80% of polyoxyethylene hydrophilic units in the molecule and the polyoxypropylene hydrophobic base has a molecular weight between 950 to 1750.

* * * * *